United States Patent
Tabuchi et al.

(10) Patent No.: US 8,062,863 B2
(45) Date of Patent: Nov. 22, 2011

(54) NUCLEIC ACIDS ENCODING HAMSTER 1GF-1 PROTEINS AND METHODS THEREOF

(75) Inventors: Hisahiro Tabuchi, Tokyo (JP); Saeko Tanaka, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 400 days.

(21) Appl. No.: 11/884,538

(22) PCT Filed: Feb. 21, 2006

(86) PCT No.: PCT/JP2006/303045
§ 371 (c)(1),
(2), (4) Date: Aug. 17, 2007

(87) PCT Pub. No.: WO2006/088198
PCT Pub. Date: Aug. 24, 2006

(65) Prior Publication Data
US 2009/0011453 A1 Jan. 8, 2009

(30) Foreign Application Priority Data

Feb. 21, 2005 (JP) .................................. 2005-044625
Sep. 22, 2005 (JP) .................................. 2005-275485

(51) Int. Cl.
*C12P 21/06* (2006.01)

(52) U.S. Cl. ......... 435/69.1; 435/6; 435/7.1; 435/320.1; 435/252

(58) Field of Classification Search ........................ None
See application file for complete search history.

(56) References Cited

U.S. PATENT DOCUMENTS 7,469,185 B2 * 12/2008 Mendrick et al. ................ 702/19
2002/0102650 A1 8/2002 Hunt et al.
2006/0003958 A1 * 1/2006 Melville et al. .................. 514/44

FOREIGN PATENT DOCUMENTS

| WO | WO 89/05822 A1 | 6/1989 |
| WO | WO 00/40612 A1 | 7/2000 |
| WO | WO 00/40613 A1 | 7/2000 |

OTHER PUBLICATIONS

Shimatsu et al., "Mosaic Evolution of the Insulin-like Growth Factors," J. Biol. Chem., Jun. 5, 1987, 262(16):7894-7900.
European Search Report dated Aug. 6, 2010, in corresponding EP 09176322.7, 11 pages.
Pak et al., "Super-CHO—A cell line capable of autocrine growth under fully defined protein-free conditions," Cytotechnology, Jan. 1, 1996, 22:139-146.
Sunstrom et al., "Insulin-Like Growth Factor-I and Transferrin Mediate Growth and Survival of Chinese Hamster Ovary Cells," Biotechnol. Prog., Jan. 1, 2000, 16(5):698-702.
Sunstrom et al., "Regulated autocrine growth of CHO cells," Cytotechnology, Oct. 2000, 34(1-2):39-46.
Sunstrom et al., "Recombinant insulin-like growth factor-I (IGF-I) production in Super-HO results in the expression of IGF-I receptor and IGF-binding protein 3," Cytotechnology, Sep. 1, 1998, 28(1-3):91-99.
Partial European Search Report dated Feb. 24, 2010 in corresponding EP 09176322.7, 6 pages.
Cascieri et al., "Mutants of Human Insulin-like Growth Factor I with Reduced Affinity for the Type 1 Insulin-like Growth Factor Receptor," Biochemistry, May 3, 1988, 27(9):3229-3233.
MacAulay, V.M., "Insulin-like growth factors and cancer," Br. J. Cancer, Jan. 1, 1992, 65(3):311-320.
Stewart et al., "Growth, Differentiation, and Survival: Multiple Physiological Functions for Insulin-Like Growth Factors," Physiological Reviews, Oct. 1, 1996, 76(4):1005-1026.

* cited by examiner

*Primary Examiner* — Hope A Robinson
(74) *Attorney, Agent, or Firm* — Foley & Lardner LLP

(57) ABSTRACT

A polypeptide selected from the group consisting of: (1) a polypeptide having the amino acid sequence of SEQ ID NO: 1, and (2) a polypeptide having an amino acid sequence in which the third amino acid of the amino acid sequence of SEQ ID NO: 1 is substituted by another amino acid and having insulin-like growth factor 1 (IGF-1) activity; a DNA encoding said polypeptide; a vector containing said DNA; a host cell containing said vector; and a method for preparing a recombinant protein using said polypeptide.

21 Claims, 6 Drawing Sheets

Figure 1

Hamster IGF-1

Secreted mature hamster IGF-1 (70 amino acids)

```
  1 : tttgccacagctggaccagagaccctctgcggggctgagctggtggatgctcttcaattc
               G  P  E  T  L  C  G  A  E  L  V  D  A  L  Q  F 61 : gtgtgtggaccaaggggcttttacttcaacaagcccacaggctatggctccagcattcgg
         V  C  G  P  R  G  F  Y  F  N  K  P  T  G  Y  G  S  S  I  R 121 : agggcacctcagacaggcattgtagatgagtgctgcttccggagctgtgatctgagaaga
         R  A  P  Q  T  G  I  V  D  E  C  C  F  R  S  C  D  L  R  R 181 : ctggagatgtactgtgccccccctcaagcctacaaaatcggcccgctctatccgtgcccag
         L  E  M  Y  C  A  P  L  K  P  T  K  S  A 241 : cg
```

Figure 2

Comparison between hamster and
human IGF-1 amino acid sequences

```
                    1                    20                   34
                    |                    |                    |
         Hamster    GPETLCGAEL VDALQFVCGP RGFYFNKPTG YGSSIRRAPQ
                    ||||||||||  ||||||||  ||||||||||  ||||   |||||
         Human      GPETLCGAEL VDALQFVCGD RGFYFNKPTG YGSSSRRAPQ 67
                                                     |
         Hamster    TGIVDECCFR SCDLRRLEMY CAPLKPTKSA
                    ||||||||||  ||||||||||  ||||||   |||
         Human      TGIVDECCFR SCDLRRLEMY CAPLKPAKSA
```

Native E3E hamster IGF-1 and
active E3R, E3K, E3S hamster IGF-1

3                                        70

Hamster IGF1    GPETLCGAEL VDALQFVCGP..........

↓

Variation in amino acid charge

E3E  (−)  native form

E3R  (+)  active form

E3K  (+)  active form

E3S  (±)  active form

Hamster IGF-1 (70 amino acids)-expression plasmid
containing triple hamster IGF-1 genes Triple transferred
hamster IGF1 genes

1) E3E
2) E3S
3) E3K

Amounts of anti-IL6R antibodies produced in fed-batch cultures

Amounts of anti-IL6R antibodies produced in fed-batch cultures

Amounts of anti-IL6R antibodies produced in fed-batch cultures of the best strains Amounts of anti-IL6R antibodies produced in fed-batch cultures

NUCLEIC ACIDS ENCODING HAMSTER IGF-1 PROTEINS AND METHODS THEREOF

CROSS REFERENCE TO RELATED APPLICATIONS

This application is a National Stage application of PCT/JP2006/303045, filed Feb. 21, 2006, which claims priority from Japanese patent applications JP 2005-044624, Feb. 21, 2005, and JP 2005-275485, filed Sep. 22, 2006.

TECHNICAL FIELD

The present invention relates to novel hamster IGF-1 polypeptides. The present invention also relates to methods for efficiently and inexpensively producing desired recombinant proteins using the novel IGF-1 polypeptides.

BACKGROUND ART

Animal cells have been frequently used as host cells for producing recombinant proteins because animal cells allow complex post-translational modification and/or folding that could not be achieved with bacterial cells when they are used for producing pharmaceutically useful proteins by genetic engineering techniques.

When a natural protein produced by an animal cell was to be obtained by culturing the animal cell or when a desired protein was to be prepared by culturing an animal cell transformed with a gene encoding the desired protein, the culture medium had to be supplemented with 5-20% of an extract, normally derived from a mammal for the growth of the animal cell, specifically a serum such as fetal calf serum, in addition to basic nutrients such as salts, sugars, amino acids and vitamins. However, this entailed the following disadvantages: 1) such sera derived from mammals are expensive, 2) stable growth can not be achieved due to variation in quality among lots, 3) there is a possibility of contamination with viruses and/or mycoplasmas, and 4) the isolation/purification of the desired protein as the cell product from the culture medium may be complicated. Thus, there has been a need for a technique capable of inexpensively producing recombinant proteins by culturing animal cells in serum-free media.

In order to produce a protein in a serum-free medium, a growth factor contained in a serum must be added, and when e.g., CHO cells are cultured, cell proliferation and survival rate are improved to achieve long-term culture and/or large-scale culture, normally by adding human IGF-1 (insulin-like growth factor 1).

The mature form of IGF-1 is a single chain polypeptide of 70 amino acids discovered as a polypeptide having insulin-like activities and has a structure similar to that of proinsulin. IGF-1 has a cell-proliferating effect and insulin-like metabolic activity and counts as one of the most important growth factors for the growth of individuals. IGF-1 is produced in the liver under the action of a growth hormone (GH) secreted from the hypophysis and thought to promote the growth of a remote target bone tissue and to show metabolic activity in muscle and adipose cells.

Recently, IGF-1 has been produced in various cell culture systems, and IGF-1 was reported to have not only a proliferating effect on these cells but also various physiological activities, in addition to the endocrine effects as described above. Moreover, noting the cell proliferation-promoting effect of IGF-1, a method for preparing a recombinant protein by transferring a DNA encoding a polypeptide having a proliferation-promoting effect such as human IGF-1 into an animal cell culture system producing the recombinant protein was proposed (US 2002/0102650 A1).

Various growth factors such as IGF-1 are used as recombinants derived from humans, but these are very expensive, and it is therefore desirable to decrease a content of IGF-1 to reduce production costs.

DISCLOSURE OF THE INVENTION

Problems to be Solved by the Invention

An object of the present invention is to obtain a novel IGF-1 polypeptide having a strong cell proliferation-promoting activity at low production cost. Another object of the present invention is to prepare a host animal cell capable of efficiently and inexpensively producing a recombinant protein by using a DNA encoding the novel IGF-1 polypeptide. Still another object of the present invention is to provide a method for preparing a recombinant protein by using the host animal cell.

Means to Solve the Problems

As a result of careful studies to attain the above objects, we discovered a novel insulin-like growth factor 1 (IGF-1) polypeptide derived from hamster and found that the novel IGF-1 polypeptide has a remarkable cell proliferation-promoting effect in animal cell cultures, and thereby we accomplished the present invention.

Accordingly, the present invention provides the following:

1. A polypeptide selected from the group consisting of:
   (1) a polypeptide having the amino acid sequence of SEQ ID NO: 1, and
   (2) a polypeptide having an amino acid sequence in which the third amino acid of the amino acid sequence of SEQ ID NO: 1 is substituted by another amino acid and having insulin-like growth factor 1 (IGF-1) activity.
2. The polypeptide as defined in 1 above wherein the third amino acid is substituted by serine.
3. The polypeptide as defined in 1 above wherein the third amino acid is substituted by lysine
4. A DNA encoding the polypeptide as defined in 1 above.
5. A vector containing the DNA as defined in 4 above.
6. A host cell containing the vector as defined in 5 above.
7. The host cell as defined in 6 above, which is a CHO cell.
8. A method for preparing the polypeptide as defined in 1 above using the host cell as defined in 6 or 7 above.
9. An antibody binding to the polypeptide as defined in 1 above.
10. A cell for producing a desired protein into which a DNA encoding the polypeptide as defined in 1 above and a DNA encoding the desired protein are transferred.
11. The cell as defined in 10 above wherein the DNA encoding the polypeptide as defined in 1 above and the DNA encoding the desired protein are simultaneously transferred by a single vector.
12. The cell as defined in 10 above wherein the DNA encoding the polypeptide as defined in 1 above and the DNA encoding the desired protein are separately transferred by multiple vectors.
13. The cell as defined in any one of 10 to 12 above, which is a CHO cell.
14. A method for preparing a desired protein, comprising culturing the cell as defined in any one of 10 to 13 above.
15. A culture medium containing the polypeptide as defined in 1 above.

16. The culture medium as defined in 15 above wherein the polypeptide as defined in 1 above is added to the medium.

17. The culture medium as defined in 15 above wherein the polypeptide as defined in 1 above is secreted from a host cell.

18. The culture medium as defined in any one of 15 to 17 above, which is a serum-free medium or a medium free from any component derived from mammals except for the polypeptide as defined in 1 above.

19. A method for preparing a desired protein, comprising culturing a CHO cell using the culture medium as defined in any one of 15 to 18 above.

20. A method for preparing a cell for use in the preparation of a desired protein, comprising the steps of:
    (a) transferring a DNA encoding the desired protein into a CHO cell, and
    (b) transferring a DNA encoding IGF-1 into the cell prepared in step (a).

21. A method for preparing a cell for use in the preparation of a desired protein, comprising the steps of:
    (a) transferring a DNA encoding the desired protein into a CHO cell,
    (b) selecting a cell expressing the desired protein from the cell prepared in step (a), and
    (c) transferring a DNA encoding IGF-1 into the cell selected in step (b).

22. A method for preparing a cell for use in the preparation of a desired protein, comprising the steps of:
    (a) transferring a DNA encoding the desired protein and a DNA encoding IGF-1 simultaneously into a CHO cell, and
    (b) selecting a cell expressing the desired protein from the cell prepared in step (a).

23. The method as defined in 22 above wherein the DNA encoding the desired protein and the DNA encoding IGF-1 are simultaneously transferred into a CHO cell using a single vector containing the DNA encoding the desired protein and the DNA encoding IGF-1.

24. A method for preparing a cell for use in the preparation of a desired protein, comprising the steps of:
    (a) transferring a DNA encoding IGF-1 into a CHO cell, and
    (b) transferring a DNA encoding the desired protein into the cell prepared in step (a).

25. A method for preparing a cell for use in the preparation of a desired protein, comprising the steps of:
    (a) transferring a DNA encoding IGF-1 into a CHO cell,
    (b) transferring a DNA encoding the desired protein into the cell prepared in step (a), and
    (c) selecting a cell expressing the desired protein from the cell prepared in step (b).

26. The method as defined in any one of 20 to 25 above wherein IGF-1 is the polypeptide as defined in 1 above.

27. A method for screening a cell for use in the preparation of a desired protein, comprising the steps of:
    (a) transferring a DNA encoding the desired protein into a CHO cell,
    (b) selecting a cell expressing the desired protein from the cell prepared in step (a),
    (c) transferring a DNA encoding IGF-1 into the cell selected in step (b), and
    (d) selecting a cell expressing the desired protein and IGF-1 from the cell prepared in step (c).

28. The screening method as defined in 27 above wherein IGF-1 is the polypeptide as defined in 1 above.

BRIEF EXPLANATION OF THE DRAWINGS

FIG. 1 shows the nucleotide sequence (SEQ ID NO: 2) and amino acid sequence (SEQ ID NO: 1) of the hamster IGF-1 gene derived from CHO cells of the present invention.

FIG. 2 shows a comparison between the amino acid sequences of the hamster IGF-1 (SEQ ID NO: 1) derived from CHO cells of the present invention and human IGF-1 (SEQ ID NO: 9).

THE MOST PREFERRED EMBODIMENTS OF THE INVENTION

Figures 3, 4:
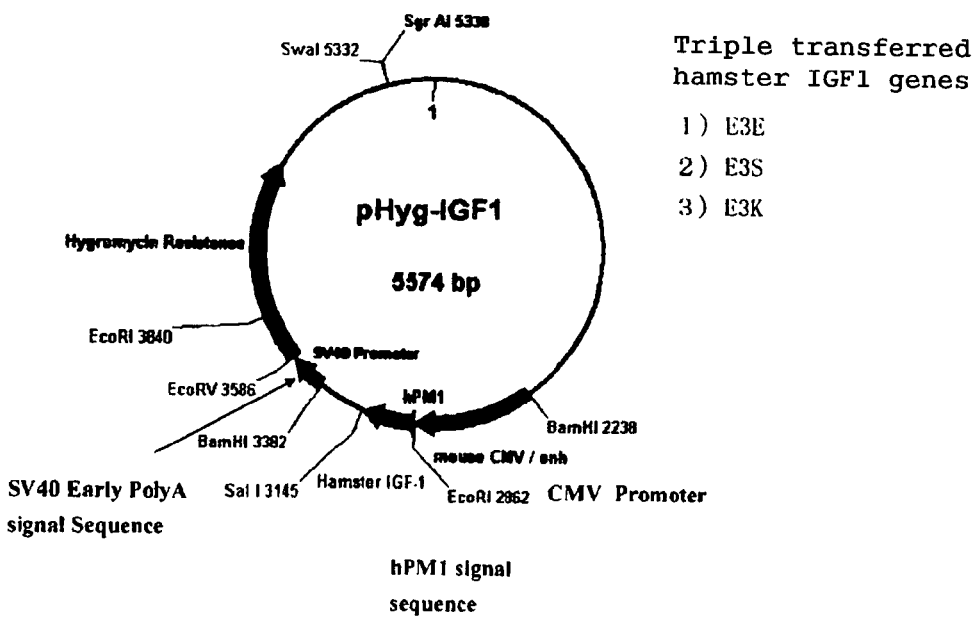
FIG. 3 shows activated hamster IGF-1 (Residues 1-20 of SEQ ID NO: 1) variants in which the negatively charged amino acid E at position 3 from the N-terminus of 70 amino acids of hamster IGF-1 was changed into R, K and S for positively shifting the polarity. (+) represents a positively charged amino acid, (−) represents a negatively charged amino acid, and (±) represents a neutral amino acid.
FIG. 4 shows a plasmid for expressing modified hamster IGF-1.

The polypeptide of the present invention is preferably secreted mature hamster IGF-1 having the amino acid sequence shown in FIG. 1 and SEQ ID NO: 1, but may also be precursor hamster IGF-1.

The polypeptide of the present invention also includes a polypeptide having an amino acid sequence in which the third amino acid of the amino acid sequence of hamster IGF-1 shown in SEQ ID NO: 1 is substituted by another amino acid and having insulin-like growth factor 1 (IGF-1) activity. The third amino acid may be substituted by any amino acid not specifically limited, but preferably serine, lysine, or aspartate, especially serine or lysine.

As used herein, the expression "having insulin-like growth factor 1 (IGF-1) activity" refers to having a proliferation-promoting activity and/or survival rate-increasing activity for animal cells.

As used herein, the term "polypeptide" is sometimes? synonymous with "protein".

The polypeptide of the present invention can be prepared as a recombinant polypeptide or a natural polypeptide by a method known to those skilled in the art. The recombinant polypeptide can be prepared by harvesting transformants from a suitable host cell transformed with a suitable expression vector carrying a DNA encoding the polypeptide of the present invention and then purifying thus obtained extracts by ion exchange, reverse-phase, gel filtration or like chromatography, or affinity chromatography using a column coupled with an antibody against the polypeptide of the present invention, or a combination of these columns.

When the polypeptide of the present invention is expressed as a fusion protein with a glutathione S transferase protein or as a recombinant protein having multiple histidines in a host cell (e.g., animal cell or *E. coli*), the expressed recombinant protein can be purified by a glutathione column or nickel column.

After purification of the fusion protein, regions other than the desired polypeptide in the fusion protein can be cleaved by thrombin or factor Xa or the like and removed, if desired.

The natural polypeptide can be isolated by a method well-known to those skilled in the art, e.g., by purifying the extracts of a tissue or cell expressing the polypeptide of the present invention through an affinity column coupled with an antibody binding to the hamster IGF-1 polypeptide described below. The antibody may be polyclonal or monoclonal.

The present invention also provides a DNA encoding the hamster IGF-1 of the present invention. The DNA of the present invention can be used for producing the polypeptide of the present invention as described above in vivo or in vitro. The DNA of the present invention may be in any form so far as it can encode the polypeptide of the present invention. That is, it may be any of a cDNA synthesized from mRNA, or a genomic DNA, or a chemically synthesized DNA. A DNA having any nucleotide sequence based on the degeneracy of the genetic code is included so far as it can encode the polypeptide of the present invention.

The DNA of the present invention can be prepared by a method known to those skilled in the art. For example, it can be prepared by constructing a cDNA library from a cell expressing the polypeptide of the present invention and hybridizing it with a part of the sequence of the DNA of the present invention (e.g., SEQ ID NO: 2) as a probe. The cDNA library may be prepared by the method described in e.g., Sambrook, J. et al., Molecular Cloning, Cold Spring Harbor Laboratory Press (1989) or may also be a commercially available DNA library. It can also be constructed by preparing an RNA from a cell expressing the polypeptide of the present invention, synthesizing oligo DNAs on the basis of the sequence of the DNA of the present invention, and amplifying the cDNA encoding the polypeptide of the present invention by PCR reaction using them as primers.

Specifically, the following procedure can be followed. First, mRNA is isolated from a cell, tissue, organ or the like expressing the polypeptide of the present invention. The isolation of mRNA is performed by preparing total RNA by a known method, e.g., guanidine ultracentrifugation (Chirgwin, J. M. et al., Biochemistry (1979) 18, 5294-5299), AGPC method (Chomczynski, P. and Sacchi, N., Anal. Biochem. (1987) 162, 156-159), etc., and purifying mRNA from the total RNA by using mRNA Purification Kit (Pharmacia) or the like. Alternatively, mRNA can be directly prepared by using QuickPrep mRNA Purification Kit (Pharmacia).

A cDNA is synthesized from the resulting mRNA using a reverse transcriptase. A cDNA can also be synthesized using AMV Reverse Transcriptase First-strand cDNA Synthesis Kit (Seikagaku Corporation) or the like. A cDNA can also be synthesized and amplified by 5'-RACE (Frohman, M. A. et al., Proc. Natl. Acad. Sci. U.S.A. (1988) 85, 8998-9002; Belyavsky, A. et al., Nucleic Acids Res. (1989) 17, 2919-2932) using 5'-Ampli FINDER RACE Kit (Clontech) and polymerase chain reaction (PCR) with the primers described herein.

In the Examples below, a cDNA encoding the hamster IGF-1 polypeptide was obtained by PCR cloning. PCR primers were designed using regions conserved among known rat/mouse/human IGF-1 gene sequences.

A desired DNA fragment is prepared from the resulting PCR product and fused to a vector DNA. Thus, a recombinant vector is prepared and transferred into *E. coli* or the like and colonies are selected to prepare a desired recombinant vector. The nucleotide sequence of the desired DNA can be confirmed by a known method such as e.g., dideoxynucleotide chain termination.

A genomic DNA can be isolated by screening a genomic DNA library using thus obtained cDNA as a probe.

In the DNA of the present invention, a nucleotide sequence with higher expression efficiency can be designed in consideration of the codon usage frequency of the host used for expression (Grantham, R. et al., Nucleic Acids Research (1981) 9, r43-74). Moreover, the DNA of the present invention can be modified by use of commercially available kits or known methods. Modifications include e.g., digestion with restriction enzymes, insertion of synthetic oligonucleotides or suitable DNA fragments, addition of linkers, insertion of initiation codons (ATG) and/or stop codons (TAA, TGA, or TAG), etc.

The present invention also provides a vector containing the DNA of the present invention. The vector of the present invention is useful for maintaining the DNA of the present invention in a host cell or for expressing the polypeptide of the present invention.

The vector is not specifically limited so far as it contains "ori" for amplifying the vector in *E. coli* (e.g., JM109, DH5α, DH10α, HB101, XL1-blue) so that it is prepared in a large quantity by massive amplification in *E. coli* and a gene for selecting transformed *E. coli* (e.g., a drug-resistant gene discernable by some drug (ampicillin, tetracycline, kanamycin, chloramphenicol)) when the host is e.g. *E. coli*. Examples of vectors include M13 vectors, pUC vectors, pBR322, pBluescript, pCR-Script, etc. In addition to the vectors mentioned above, e.g., pGEM-T, pDIRECT, pT7 and the like are also included for the purpose of subcloning or excising a cDNA. When the vector is used to produce the polypeptide of the present invention, an expression vector is especially useful. The expression vector must have the characteristics described above allowing the vector to be amplified in *E. coli* when the expression in e.g., *E. coli* is desired, and it must further contain promoters for efficient expression in *E. coli*, e.g., lacZ promoter (Ward et al., Nature (1989) 341, 544-546; FASEB J. (1992) 6, 2422-2427), araB promoter (Better et al., Science (1988) 240, 1041-1043), or T7 promoter when the host is *E. coli* such as JM109, DH5α, DH10α, HB101, XL1-blue. Such vectors include pGEX-5X-1 (Pharmacia), "QIAexpress system®" (Qiagen), pEGFP, or pET (in this case, the host is preferably BL21 expressing T7 RNA polymerase) in addition to the vectors mentioned above.

The vector may also contain a signal sequence for secreting the polypeptide. When the polypeptide is to be produced in the periplasm of *E. coli*, the pelB signal sequence (Lei, S. P. et al J. Bacteriol. (1987) 169, 4379) can be used as the signal sequence for secreting the polypeptide. The transfer of the vector into a host cell can be performed by e.g. calcium chloride-mediated transformation or electroporation.

In addition to *E. coli*, vectors used to e.g., prepare the polypeptide of the present invention include e.g., expression vectors derived from mammals (e.g., pcDNA3 (Invitrogen) or pEF-BOS (Nucleic Acids. Res. 1990, 18, p 5322), pEF, pCDM8), expression vectors derived from insect cells (e.g., "BAC-to-BAC™ baculovirus expression system" (pBacPAK8 from Invitrogen)), expression vectors derived from plants (e.g., pMH1, pMH2), expression vectors derived from animal viruses (e.g., pH SV, pMV, pAdexLcw), expression vectors derived from retroviruses (e.g., pZIpneo), expression vectors derived from yeasts (e.g., "*Pichia* Expression Kit" (Invitrogen), pNV11, SP-Q01), expression vectors derived from *Bacillus subtilis* (e.g., pPL608, pKTH50), etc.

When the expression in animal cells such as CHO cells, COS cells, NIH3T3 cells is desired, the vector must contain promoters necessary for the expression within the cells, e.g., SV40 promoter (Mulligan et al., Nature (1979) 277, 108), MMLV-LTR promoter, EF1α promoter (Mizushima et al., Nucleic Acids Res. (1990) 18, 5322), RSV promoter, CMV promoter, and more preferably it further contains a gene for selecting transformation into the cells (e.g., a drug-resistant gene discernible by drugs (neomycin, G418, hygromycin, puromycin)). Vectors having such properties include, e.g., pMAM, pDR2, pBK-RSV, pBK-CMV, pOPRSV, pOP13, etc.

When it is desirable to stably express a gene and amplify the number of copies of the gene in cells, CHO cells lacking the pathway of nucleic acid synthesis can be transformed with a vector containing the DHFR gene complementing it (e.g., pCHOI) and amplified by methotrexate (MTX), or when it is desirable to transiently express a gene, COS cells carrying a gene encoding the SV40 T-antigen on their chromosome can be transformed with a vector containing the origin of replication for SV40 (pCD, etc.). Other suitable origins of replication include sequences derived from polyomaviruses, adenoviruses, bovine papilloma virus (BPV), etc. To amplify the number of copies of the gene in a host cell system, the expression vector can further contain selectable markers such as aminoglycoside transferase (APH) gene, thymidine kinase (TK) gene, *E. coli* xanthine-guanine phosphoribosyl transferase (Ecogpt) gene, dihydrofolate reductase (dhfr) gene, etc.

When the DNA of the present invention is to be expressed in vivo in an animal, a suitable vector containing the DNA of the present invention can be transferred into the living body by retrovirus-, liposome-, cationic liposome- or adenovirus-mediated transformation. Suitable vectors include, but not limited to, e.g., adenoviral vectors (e.g., pAdexlcw) and retroviral vectors (e.g., pZIPneo). General gene manipulation such as insertion of the DNA of the present invention into the vector can be performed by conventional methods (Molecular Cloning, 5.61-5.63). Administration into the living body may be performed ex vivo or in vivo.

The present invention also provides a host cell transformed with the vector of the present invention. The host cell to be transformed with the vector of the present invention is not specifically limited, and various animal cells such as e.g., *E. coli* and CHO cells can be used. The host cell of the present invention can be used as e.g., a production system for preparing or expressing the polypeptide of the present invention. Production systems for preparing polypeptides include in vitro and in vivo production systems. In vitro production systems include those using eukaryotic cells or prokaryotic cells.

When eukaryotic cells are used, e.g., animal cells, plant cells and fungal cells can be used as hosts. Known animal cells include mammal cells, e.g., CHO (J. Exp. Med. (1995) 108, 945), COS, 3T3, myeloma, BHK (baby hamster kidney), HeLa, Vero; amphibian cells, e.g. *Xenopus oocytes* (Valle, et al., Nature (1981) 291, 358-340); or insect cells, e.g., Sf9, Sf21, Tn5. Among CHO cells, CHO cells deficient in the DHFR gene, i.e., CHO dhfr- (Proc. Natl. Acad. Sci. USA (1980) 77, 4216-4220) or CHO-K1 (Proc. Natl. Acad. Sci. USA (1968) 60, 1275) can be preferably used. When large-scale expression in animal cells is desired, CHO cells are especially preferred. The vector can be transferred into the host cells by e.g., calcium phosphate-mediated transfection, DEAE dextran-mediated transfection, cationic liposome DOTAP-mediated transfection (Boehringer Mannheim), electroporation, lipofection, etc.

Plant cells known as polypeptide-producing systems include e.g., cells derived from *Nicotiana tabacum*, which can be used as callus cultures. Aquatic plant cultures (Biolex) are also effective. Known fungal cells include yeasts, e.g., genus *Saccharomyces*, e.g., *Saccharomyces cerevisiae*; filamentous fungi, e.g., genus *Aspergillus*, e.g., *Aspergillus niger*.

When prokaryotic cells are used, production systems using bacterial cells are known. Known bacterial cells include *E. coli* (*E. coli*), e.g., JM109, DH5α, DH10α, HB101, etc., as well as *Bacillus subtilis*.

The polypeptide can be obtained by transforming these cells with the desired DNA and culturing the transformed cells in vitro. Incubation can be performed by known methods. For example, culture media that can be used for animal cells include, e.g., DMEM, MEM, RPMI1640, IMDM. The media can be supplemented with serum such as fetal calf serum (FCS) or can be serum-free. The pH during incubation is preferably about 6-8. Incubation is normally performed at about 30-40° C. for about 15-240 hours, and if desired, the media are replaced, aerated or stirred.

In vivo polypeptide-producing systems include, e.g., production systems using animals or plants. These animals or plants are transformed with the desired DNA and the polypeptide is produced in the animals or plants and harvested. As used herein, the term "host" is intended to include these animals and plants.

When animals are used, production systems using mammals and insects are included. Mammals that can be used include goat, pig, sheep, mouse, and cow (Vicki Glaser, SPECTRUM Biotechnology Applications, 1993). When mammals are used, transgenic animals can be used.

For example, the desired DNA is prepared as a gene fused to a gene encoding a polypeptide produced specifically in milk such as goat β casein. Then, a DNA fragment containing the fusion gene is injected into the embryo of a goat and this embryo is implanted into a female goat. The desired polypeptide can be obtained from the milk produced by transgenic goats born from the goat impregnated with the embryo or progeny thereof. To increase the amount of the polypeptide-containing milk produced by the transgenic goats, hormones may be used in the transgenic goats as appropriate (Ebert, K. M. et al., Bio/Technology (1994) 12, 699-702).

Insects that can be used include, e.g. silkworms. When silkworms are used, the desired polypeptide can be obtained from the body fluid of silkworms infected with a baculovirus containing a DNA encoding the desired polypeptide (Susumu, M. et al., Nature (1985) 315, 592-594).

When plants are used, tobacco can, for example, be used. When tobacco is used, a DNA encoding the desired polypeptide is inserted into a plant expression vector, e.g. pMON 530, and this vector is transferred into a bacterium such as *Agrobacterium tumefaciens*. The desired polypeptide can be obtained from leaves of tobacco, e.g., *Nicotiana tabacum* infected with this bacterium (Julian K.-C. Ma et al., Eur. J. Immunol. (1994) 24, 131-138).

Thus obtained polypeptide of the present invention can be isolated from the host cells or extracellular systems (such as culture media) and purified as a substantially pure and homogeneous polypeptide. The isolation/purification of the polypeptide can be performed by any isolation/purification method conventionally used for the purification of polypeptides. For example, the polypeptide can be isolated/purified by appropriately selecting/combining chromatography columns, filters, ultrafiltration, salting, solvent precipitation, solvent extraction, distillation, immunoprecipitation, SDS-polyacrylamide gel electrophoresis, isoelectric electrophoresis, dialysis, recrystallization, etc.

Chromatographies include e.g., affinity chromatography, ion exchange chromatography, hydrophobic chromatography, gel filtration chromatography, reverse phase chromatography, adsorption chromatography, etc. (Strategies for Protein Purification and Characterization: A Laboratory Course Manual. Ed Daniel R. Marshak et al., Cold Spring Harbor Laboratory Press, 1996). These chromatographies can be performed by using liquid phase chromatographies such as HPLC, FPLC, etc. The present invention also includes polypeptides highly purified by using these purification methods.

Optionally, a peptide can be partially removed by modifying the polypeptide by the action of a suitable polypeptide-modifying enzyme before or after it is purified. Polypeptide-modifying enzymes include, e.g., trypsin, chymotrypsin, lysyl endopeptidase, protein kinase, glucosidase, etc.

The present invention also provides an antibody binding to the polypeptide of the present invention. The antibody of the present invention is not specifically limited to any form, and may be polyclonal or monoclonal. Antisera obtained by immunizing an animal such as a rabbit with the polypeptide of the present invention, all classes of polyclonal and monoclonal antibodies, as well as human antibodies and humanized antibodies obtained by genetic engineering are also included.

The polypeptide of the present invention used as an immunizing antigen for obtaining the antibody can be obtained by using the gene sequences or amino acid sequences disclosed herein.

In the present invention, the polypeptide used as an immunizing antigen may be a whole peptide or a partial peptide of the polypeptide.

The desired polypeptide of the present invention or a fragment thereof can be obtained in vivo or in vitro by a known method from host cells described herein transformed with a known expression vector containing a gene encoding the polypeptide or a fragment thereof and can be used as the immunizing antigen. Alternatively, a cell expressing the polypeptide or a lysate thereof or a chemically synthesized polypeptide of the present invention may also be used as the immunizing antigen.

The mammal immunized with the immunizing antigen is not specifically limited, but preferably selected in consideration of compatibility with the parent cell used for cell fusion, and typically selected from rodents, lagomorphs and primates.

Suitable rodents include, e.g., mouse, rat, hamster, etc. Suitable lagomorphs include, e.g., rabbit. Suitable primates include, e.g., monkeys. Suitable monkeys include Catarrhini (old world monkey), e.g., macaque, rhesus, hamadryad, chimpanzee, etc.

The animals are immunized with the immunizing antigen according to known methods. A typical method is intraperitoneal or subcutaneous injection of the immunizing antigen into a mammal. Specifically, the immunizing antigen is diluted or suspended to an appropriate volume in PBS (Phosphate-Buffered Saline) or physiological saline and, if desired, mixed with an appropriate amount of a conventional adjuvant, e.g., Freund's complete adjuvant, and emulsified and then administered to a mammal. Preferably, an appropriate amount of the immunizing antigen is then mixed with Freund's incomplete adjuvant and administered several times every 4-21 days. A suitable carrier can be used during immunization with the immunizing antigen. The animal is immunized in this manner, and an increase in the serum level of the desired antibody is confirmed by a conventional method.

To obtain a polyclonal antibody against the polypeptide of the present invention, blood is collected from the mammal immunized with the antigen after confirming that the serum level of the desired antibody has increased. Serum is separated from this blood by a known method. Serum containing the polyclonal antibody can be used or, if desired, a fraction containing the polyclonal antibody can be further isolated from this serum and used. For example, immunoglobulin G or M can be prepared by collecting a fraction recognizing only the polypeptide of the present invention through an affinity column coupled with the polypeptide of the present invention and purifying this fraction through a protein A or protein G column.

To obtain a monoclonal antibody, immunized cells can be collected from the mammal immunized with the antigen and used for cell fusion after confirming that the serum level of the desired antibody has increased. Preferred immunized cells used for cell fusion here especially include spleen cells. Parent cells to be fused to the immunized cells preferably include mammalian myeloma cells, more preferably myeloma cells having acquired a property for selecting fused cells by a drug.

Cell fusion of the immunized cells to myeloma cells can be performed basically according to known methods, e.g., the method of Milstein et al. (Galfre, G. and Milstein, C., Methods Enzymol. (1981) 73, 3-46).

Hybridomas obtained by cell fusion are selected by incubation in a conventional selective culture medium, e.g., HAT medium (a culture medium containing hypoxanthine, aminopterin and thymidine). The incubation in the HAT medium is continued for a sufficient period to kill cells other than desired hybridomas (non-fused cells), typically, several days to several weeks. Then, hybridomas producing the desired antibody are screened by conventional limiting dilution and are cloned.

In addition to the hybridomas obtained by immunizing a non-human animal with the antigen, hybridomas producing a desired human antibody having a polypeptide-binding activity can be obtained by in vitro immunizing human lymphocytes, e.g. human lymphocytes infected with EB virus with the polypeptide, a cell expressing the polypeptide or a lysate thereof and fusing the immunized lymphocytes to permanently dividing myeloma cells derived from human, e.g. U266 (JPA SHO 63-17688).

Then, the resulting hybridoma is transplanted into the abdominal cavity of a mouse and ascites are collected from the mouse, and thus obtained monoclonal antibody can be purified by e.g., ammonium sulfate precipitation, protein A column, protein G column, DEAE ion exchange chromatography, an affinity column coupled with the polypeptide of the present invention, etc. The antibody of the present invention serves not only for the purification or detection of the polypeptide of the present invention but also as a candidate of an agonist or antagonist of the polypeptide of the present invention. It is also contemplated that this antibody can be applied to antibody therapy of diseases in which the polypeptide of the present invention is involved. When the antibody obtained is used for the purpose of administration to humans (antibody therapy), it is preferably a human antibody or humanized antibody to reduce immunogenicity.

For example, a human antibody against the polypeptide can be obtained by using hybridomas obtained by immunizing a transgenic animal having human antibody gene repertoires with the antigen polypeptide, a cell expressing the polypeptide or a lysate thereof to give antibody-producing cells and fusing them to myeloma cells (see International Publications Nos. WO92-03918, WO93-2227, WO94-02602, WO94-25585, WO96-33735 and WO96-34096).

In addition to hybridomas, the antibody can also be produced by using immunized cells such as antibody-producing immunized lymphocytes immortalized by an oncogene.

The monoclonal antibody can also be obtained as a recombinant antibody produced by using genetic engineering techniques (e.g., see Borrebaeck, C. A. K. and Larrick, J. W., THERAPEUTIC MONOCLONAL ANTIBODIES, Published in the United Kingdom by MACMILLAN PUBLISHERS LTD, 1990). The recombinant antibody is produced by transforming a host with a suitable vector containing a DNA encoding the antibody cloned from hybridomas or immunized cells such as immunized lymphocytes producing the antibody. The present invention includes this recombinant antibody.

Moreover, the antibody of the present invention may be an antibody fragment or modified antibody so far as it specifically binds to the polypeptide of the present invention. For example, antibody fragments include Fab, F (ab')2, Fv or single chain Fv (scFv) in which the heavy and light chain Fv fragments are joined via a suitable linker (Huston, J. S. et al., Proc. Natl. Acad. Sci. U.S.A. (1988) 85, 5879-5883). Specifically, the antibody is treated with an enzyme, e.g., papain or pepsin to produce antibody fragments or genes encoding these antibody fragments are constructed and introduced into an expression vector and then expressed in a suitable host cell (e.g., see Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Modified antibodies including antibodies conjugated with various molecules such as polyethylene glycol (PEG) can also be used. These modified antibodies are also included in the "antibody" of the present invention. Such modified antibodies can be obtained by chemically modifying the antibody obtained. These methods have already been established in this field of the art.

The antibody of the present invention can also be obtained by using a known technique as a chimeric antibody consisting of the variable regions from a non-human antibody and the constant regions from a human antibody or a humanized antibody consisting of the CDRs (complementarity-determining regions) from a non-human antibody and the FRs (framework regions) and constant regions from a human antibody.

The antibody obtained as above can be purified to homogeneity. The isolation/purification of the antibody used in the present invention can be performed by isolation/purification methods conventionally used for proteins. For example, the antibody can be isolated/purified by appropriately selecting/combining, but not limited to, chromatography columns for affinity chromatography or the like, filters, ultrafiltration, salting, dialysis, SDS-polyacrylamide gel electrophoresis, isoelectric electrophoresis, etc. (Antibodies: A Laboratory Manual. Ed Harlow and David Lane, Cold Spring Harbor Laboratory, 1988). The concentration of the antibody obtained as above can be determined by measuring the absorbance or Enzyme-linked immunosorbent assay (ELISA), etc.

Columns used for affinity chromatography include protein A columns and protein G columns. For example, protein A columns include Hyper D, POROS, Sepharose F. F. (Pharmacia).

Chromatographies other than affinity chromatography include, e.g., ion exchange chromatography, hydrophobic chromatography, gel filtration chromatography, reverse phase chromatography, adsorption chromatography, etc. (Strategies for Protein Purification and Characterization: A Laboratory Course Manual. Ed Daniel R. Marshak et. al., Cold Spring Harbor Laboratory Press, 1996). These chromatographies can be performed by using liquid phase chromatographies such as HPLC, FPLC, etc.

The antigen-binding activity of the antibody of the present invention can be assayed by e.g., measuring the absorbance or using Enzyme-linked immunosorbent assay (ELISA), EIA (Enzyme Immunoassay), RIA (Radioimmunoassay) or Fluorescent Antibody Assay. When ELISA is used, the polypeptide of the present invention is added to a plate on which the antibody of the present invention has been immobilized, and then a sample containing the desired antibody, e.g., the culture supernatant of an antibody-producing cell or a purified antibody is added. The antigen-binding activity can be evaluated by incubating the plate with a secondary antibody recognizing the antibody labeled with an enzyme, e.g., alkaline phosphatase and then washing it and then adding an enzyme substrate such as p-nitrophenyl phosphate and measuring the absorbance. A polypeptide fragment, e.g. C-terminal fragment or N-terminal fragment may also be used as the polypeptide. The activity of the antibody of the present invention can be evaluated by using BIAcore (Pharmacia).

The present invention provides a cell for producing a desired protein, which is transformed with a DNA encoding the polypeptide of the present invention and a DNA encoding the desired protein. This cell is useful for preparing the desired protein.

In the present invention, the desired protein is not specifically limited and may be any protein such as antibodies (natural antibodies, fragmented antibodies, chimeric antibodies, humanized antibodies, etc.), physiologically active proteins (granulocyte colony-stimulating factor (G-CSF), macrophage colony-stimulating factor (GM-CSF), erythropoietins, interferons, interleukins such as IL-1 or IL-6, t-PA, urokinase, serum albumin, blood coagulation factors, etc.), but antibodies are especially preferable.

The DNA encoding the polypeptide of the present invention and the DNA encoding the desired protein can be simultaneously transferred by a single vector or separately transferred by multiple vectors.

The cell to be transformed with the DNA encoding the polypeptide of the present invention and the DNA encoding the desired protein is not specifically limited and may be any cell, but CHO cells, especially CHO dhfr- cells are preferable.

The present invention also provides a culture medium containing the polypeptide of the present invention. The content of the polypeptide of the present invention in the medium can be appropriately determined, depending on the types of the medium used, the cells to be cultured and the desired protein to be prepared, but normally 0.1 mg/L-5 mg/L, preferably 0.2 mg/L-1 mg/L, more preferably 0.5 mg/L.

The culture medium containing the polypeptide of the present invention is useful for preparing a protein using animal cells, especially CHO cells.

The culture medium of the present invention can contain the polypeptide of the present invention, which may be externally added or excreted from host cells.

Other components in the culture medium used in the present invention may be those conventionally used in culture media for cells (preferably, animal cells), normally including amino acids, vitamins, lipid factors, energy sources, osmoregulators, iron sources, pH buffers. The contents of these components are normally in the ranges of suitably 0.05-1500 mg/L amino acids, 0.001-10 mg/L vitamins, 0-200 mg/L lipid factors, 1-20 g/L energy sources, 0.1-10000 mg/L osmoregulators, 0.1-500 mg/L iron sources, 1-10000 mg/L pH buffers, 0.00001-200 mg/L minor metal elements, 0-5000 mg/L surfactants, 0.05-10000 µg/L growth cofactors and 0.001-50 mg/L nucleosides, but are not limited to these ranges and can be appropriately determined depending on the type of the cell cultured, the type of the desired protein, etc.

In addition to the components above, e.g., minor metal elements, surfactants, growth cofactors, nucleosides and the like may also be added.

Specifically, the culture medium can contain e.g., amino acids such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, L-valine, etc., preferably L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine; vitamins such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin B12, ascorbic acid, etc., preferably biotin, folic acid, lipoic acid, amide nicotinate, calcium pantothenate, pyridoxal hydrochloride, riboflavin, thiamine hydrochloride, vitamin B12, ascorbic acid; lipid factors such as choline chloride, choline tartrate, linoleic acid, oleic acid, cholesterol, etc., preferably choline chloride; energy sources such as glucose, galactose, mannose, fructose, etc., preferably glucose; osmoregulators such as sodium chloride, potassium chloride, potassium nitrate, etc., preferably sodium chloride; iron sources such as iron EDTA, iron citrate, ferrous chloride, ferric chloride, ferrous sulfate, ferric sulfate, ferric nitrate, etc., preferably ferric chloride, iron EDTA, iron citrate; and pH buffers such as sodium bicarbonate, calcium chloride, sodium dihydrogen phosphate, HEPES, MOPS, etc., preferably sodium bicarbonate.

In addition to the components mentioned above, the culture medium can contain e.g., minor metal elements such as copper sulfate, manganese sulfate, zinc sulfate, magnesium sulfate, nickel chloride, tin chloride, magnesium chloride, sodium silicite, etc., preferably copper sulfate, zinc sulfate, magnesium sulfate; surfactants such as Tween™80 (polyoxyethylene sorbitan monooleate), Pluronic™F68 (polyoxyethylene-olyoxypropylene block copolymer); growth cofactors such as recombinant insulin, recombinant IGF-1, recombinant EGF, recombinant FGF, recombinant PDGF, recombinant TGF-α, ethanolamine hydrochloride, sodium selenite, retinoic acid, putrescine hydrochloride, etc., preferably sodium selenite, ethanolamine hydrochloride, recombinant IGF-1, putrescine hydrochloride; and nucleosides such as deoxyadenosine, deoxycytidine, deoxyguanosine, adenosine, cytidine, guanosine, uridine, etc. In preferred examples of the present invention described above, the culture medium can contain antibiotics such as streptomycin, penicillin G potassium and gentamicin; and pH indicators such as phenol red.

The culture medium can also contain fish extracts or enzymatically digested fish.

The pH of the culture medium depends on the cells to be cultured, but normally is pH 6.8-7.6, and may often suitably be pH 7.0-7.4.

The culture medium can be prepared from commercially available culture media for animal cells such as e.g., D-MEM (Dulbecco's Modified Eagle Medium), D-MEM/F-12 1:1 Mixture (Dulbecco's Modified Eagle Medium: Nutrient Mixture F-12), RPMI1640, CHO—S-SFMII (Invitrogen), CHO—SF (Sigma-Aldrich), EX-CELL 301 (JRH biosciences), CD-CHO (Invitrogen), IS CHO—V (Irvine Scientific), and PF-ACF—CHO (Sigma-Aldrich).

Moreover, the culture medium of the present invention is preferably a serum-free medium or a medium free from any component derived from mammals except for the polypeptide the present invention.

The present invention also provides a method for preparing a desired protein, comprising culturing a CHO cell using the polypeptide of the present invention.

The present invention also provides a method for preparing a desired protein, by culturing a CHO cell transformed with a DNA encoding the polypeptide of the present invention and a DNA encoding the desired protein.

The CHO cell can be cultured by a method known to those skilled in the art. For example, it can be normally cultured in an atmosphere at a $CO_2$ concentration of 0-40%, preferably 2-10% in the gas phase, at 30-39° C., preferably about 37° C. for 1-28 days.

Various bioreactors for animal cell cultures can be used, e.g. fermenter-type tank bioreactors, airlift bioreactors, culture flask bioreactors, spinner flask bioreactors, microcarrier bioreactors, fluidized-bed bioreactors, hollow fiber bioreactors, roller bottle bioreactors, packed-bed bioreactors, etc.

The present invention also provides a method for preparing a cell for use in the preparation of a desired protein, comprising the steps of:

(a) transferring a DNA encoding the desired protein into a CHO cell, and (b) transferring a DNA encoding IGF-1 into the cell prepared in step (a).

The present invention also provides a method for preparing a cell for use in the preparation of a desired protein, comprising the steps of:

(a) transferring a DNA encoding the desired protein into a CHO cell, (b) selecting a cell expressing the desired protein from the cell prepared in step (a), and (c) transferring a DNA encoding IGF-1 into the cell selected in step (b).

The present invention also provides a method for preparing a cell for use in the preparation of a desired protein, comprising the steps of:

(a) transferring a DNA encoding the desired protein and a DNA encoding IGF-1 simultaneously into a CHO cell, and (b) selecting a cell expressing the desired protein from the cell prepared in step (a).

When a DNA encoding the desired protein and a DNA encoding IGF-1 are simultaneously transferred into a CHO cell in the method above, the DNA encoding the desired protein and the DNA encoding IGF-1 may be simultaneously transferred by separate vectors or may be simultaneously transferred by a single vector containing the DNA encoding the desired protein and the DNA encoding IGF-1. They are preferably simultaneously transferred using a single vector.

The present invention also provides a method for preparing a cell for use in the preparation of a desired protein, comprising the steps of:

(a) transferring a DNA encoding IGF-1 into a CHO cell, and (b) transferring a DNA encoding the desired protein into the cell prepared in step (a).

The present invention also provides a method for preparing a cell for use in the preparation of a desired protein, comprising the steps of:

(a) transferring a DNA encoding IGF-1 into a CHO cell,
(b) transferring a DNA encoding the desired protein into the cell prepared in step (a), and
(c) selecting a cell expressing the desired protein from the cell prepared in step (b).

That is, a DNA encoding the desired protein and a DNA encoding IGF-1 can be transferred into a CHO cell in any order, but it is preferable to transfer a DNA encoding IGF-1 and a DNA encoding the desired protein simultaneously or to transfer a DNA encoding the desired protein and then a DNA encoding IGF-1 because the expression level of the desired protein can be readily controlled.

In the various methods for preparing a cell for use in the preparation of a desired protein, IGF-1 is preferably the polypeptide of the present invention.

The present invention also provides a method for screening a cell for use in the preparation of a desired protein, comprising the steps of:

(a) transferring a DNA encoding the desired protein into a CHO cell,
(b) selecting a cell expressing the desired protein from the cell prepared in step (a),
(c) transferring a DNA encoding IGF-1 into the cell selected in step (b), and
(d) selecting a cell expressing the desired protein and IGF-1 from the cell prepared in step (c).

In the screening method above, IGF-1 is preferably the polypeptide of the present invention.

The gene encoding IGF-1 used in the methods for preparing a cell for use in the preparation of a desired protein of the present invention or the method for screening a cell for use in the preparation of a desired protein is not specifically limited, and may be IGF-1 derived from any animal such as human, mouse, rat, hamster, but preferably hamster IGF-1. IGF-1 sequences other than hamster IGF-1 are described in Nucleic Acids Res. 14 (20), 7873-7882 (1986) and J. Biol. Chem. 262 (16), 7894-7900 (1987).

As shown in the Example below, we demonstrated that antibody-producing cells having ideal growth behavior in cultures in the absence of IGF-1 can be established by transferring a DNA encoding the polypeptide of the present invention into cells established for producing antibodies to allow them to express activated IGF-1. Antibody-producing cells transformed with the polypeptide of the present invention showed excellent proliferation potency and survival rate as well as excellent results in the amounts of antibodies produced. The present invention is industrially very useful because it can be applied to cells producing any desired protein, especially antibody-producing cells.

The following examples further illustrate the present invention without, however, limiting the invention thereto. Various changes and modifications can be made by those skilled in the art, and such changes and modifications are also included in the present invention.

EXAMPLES

Example 1

Cloning of a cDNA Encoding Hamster IGF-1

(1) Synthesis of the cDNA

Total RNA was extracted from anti-IL-6R antibody-producing cells (JPA HEI 8-99902, Reference example 2) obtained by transforming an anti-interleukin 6 receptor (IL-6R) antibody gene into CHO-DXB11 cells. The cDNA was synthesized from the resulting mRNA.

Specifically, the following procedure was followed. About $5 \times 10^6$ CHO cells in the growth phase 72 hours after subculture were obtained in a state packed at the bottom of a centrifuge tube containing no culture fluid by centrifugation at 4° C., 1,000 rpm for 5 minutes, and then quickly lysed by pipetting in 4 ml of Sepasol-RNA I prewarmed to 65° C., and allowed to stand at room temperature for 5 minutes. The tube was further thoroughly stirred with 0.8 ml of chloroform in a vortex mixer, and then allowed to stand at room temperature for 3 minutes. After centrifugation at 4° C., 7,000 rpm for 5 minutes in a cooling centrifuge Avanti™ J25 (BECKMAN), the upper layer was carefully collected and transferred to a fresh 15 ml-tube. The tube was thoroughly stirred with 4 ml of 2-propanol in a vortex mixer, and then allowed to stand at room temperature for 10 minutes. After centrifugation at 4° C., 7,000 rpm for 10 minutes, the supernatants were completely removed to give RNA pellets. The wall face of the centrifugal tube was thoroughly rinsed with 4 ml of 75% ethanol, and the tube was centrifuged at 4° C., 7,000 rpm for 5 minutes. After the supernatants were completely removed, the tube was further rinsed with 4 ml of 100% ethanol. After centrifugation at 4° C., 7,000 rpm for 5 minutes to give RNA pellets, the tube was allowed to stand at room temperature for 30 minutes. The RNA pellets were air-dried and completely lysed by pipetting in 100 µl of DEPC-Water. Further, total RNA was purified according to the protocol of RNeasy Mini Kit. The concentration of 30 µl of total RNA thus obtained was determined using a spectrophotometer DU640, and the RNA concentration was calculated as an absorbance of 1 OD=40 µg/ml at a wavelength of 260 nm. The high-purity total RNA in an amount of 5 µg was used for cDNA synthesis. The high-purity total RNA in an amount of 5 µg was prepared to 10 µl with DEPC-Water, and then completely mixed with 1 µl of HPLC grade 100 pmol/µl T7-(T)$_{24}$ primer added by pipetting and then the mixture was spun down. To anneal the primer, the mixture was heated at 70° C. for 10 minutes, and then quickly spun down and chilled on ice. After 2 minutes on ice, 4µl of 5×First-strand buffer, 2 µl of 0.1 M DTT, and 1 µl of 10 mM dNTP Mix were added by pipetting, and the mixture was spun down at 4° C. and placed on ice. Two minutes after starting incubation on a heat block at 42° C., 2 µl of SuperScript™II Reverse Transcriptase was added by pipetting to start a First-strand synthesis reaction. After 60 minutes, the mixture was quickly spun down, and placed on ice. To subsequently perform a Second-strand synthesis reaction, 91 µl of DEPC-Water, 30 µl of 5×Second-strand buffer, 3 µl of 10 mM dNTP Mix, 1 µl of E. coli DNA ligase, 4 µl of E. coli DNA polymerase, and 1 µl of E. coli RNase H were successively added by pipetting, and the mixture was spun down at 4° C., and placed on ice. The mixture was incubated at 16° C. for 120 minutes to perform Second-strand synthesis. After 2 hours, 2µl of T4 DNA polymerase was added, and after further incubation for 5 minutes, the mixture was quickly spun down, and placed on ice. The mixture was vortexed with 152 µl of 25:24:1 phenol:chloroform:isoamyl alcohol for 30 seconds, and then spun down, and further mixed by pipetting, and applied on a Phase Lock Gel™ tube preliminarily centrifuged for 1 minutes and packed with a gel. After centrifugation at 4° C., 15,000 rpm for 2 minutes, the aqueous layer was transferred to a fresh 1.5 ml-Eppendorf tube, and thoroughly vortexed with 0.5 µl of Pellet Paint ® and 76 µl of a 7.5M ammonium acetate solution successively added. The mixture was vortexed with 600 µl of 99.5% ethanol for 30 seconds, and then allowed to stand at room temperature for 5 minutes.

The mixture was centrifuged at 4° C., 15,000 rpm for 10 minutes to give cDNA precipitates free from unreacted dNTP. The cDNA was centrifuged with 500 µl of 75% ethanol at 4° C., 15,000 rpm for 3 minutes. The mixture was desalted by washing twice and further centrifuged with 100 µl of 99.5% ethanol at 4° C., 15,000 rpm for 5 minutes, and then ethanol was completely removed. The mixture was air-dried for about 5 minutes, and then dissolved in 1.5 µof RNase free Water, and stored as a cDNA at −20° C. A 1/50 volume was used as PCR template.

(2) Cloning of a cDNA Encoding Hamster IGF-1

The hamster IGF-1 gene was obtained by PCR cloning. PCR primers were designed using regions conserved among known rat/mouse/human IGF-1 gene sequences.

Specifically, the following procedure was followed. A PCR reaction was performed using the cDNA described above as a template with a gene sequence encoding Ala at position 13 to Gly at position 19 of the N-terminus of mature rat IGF-1: 5'-gctcttcagttcgtgtgtgg (SEQ ID NO: 3) as a forward primer and the sequence of a complementary strand of a gene encoding Arg at position 50 to Arg at position 56 of the N-terminus: 5'-ctcctcagatcacagctccg (SEQ ID NO: 4) as a reverse primer. After pretreatment at 95° C., 5 minutes, 35 cycles of denaturation at 98° C., 5 seconds, annealing at 53° C., 30 seconds, and extension at 72° C., 30 seconds were repeated to amplify the desired gene, followed by extension at 72° C., 10 minutes to give a 131 bp hamster IGF-1 PCR fragment.

The nucleotide sequence of the resulting PCR fragment was examined to confirm that it is an amplified DNA of hamster IGF-1, and the sequence information was used to further continue PCR reactions. A PCR reaction was performed using the cDNA described above as template with a gene sequence encoding Thr at position 29 to Ile at position 35 of the N-terminus: 5'-acaggctatggctccagcatt (SEQ ID NO: 5) as a forward primer and the sequence of a complementary strand of a gene encoding Gln at position 85 to Arg at position 77 of the N-terminus: tgagtcttgggcatgtcagtg (SEQ ID NO: 6) as a reverse primer. After pretreatment at 95° C., 5 minutes, 35 cycles of denaturation at 98° C., 5 seconds, annealing at 53° C., 40 seconds, and extension at 72° C., 90 seconds were repeated to amplify the desired gene, followed by extension at 72° C., 10 minutes to give a 170 bp hamster IGF-1 PCR fragment. As a result, a nucleotide sequence encoding Ala at position 13 of the N-terminus to Ala at position 70 of the C-terminus of mature hamster IGF-1 was obtained.

To further obtain the N-terminal sequence, a PCR reaction was performed using the cDNA described above as template with a sequence containing t at −33 bases from the base g at the 5'-end of the N-terminus of mature rat IGF-1 to g at position 14: 5'-tgcttgctcacctttaccag (SEQ ID NO: 7) as a forward primer and the sequence of a complementary strand of a gene encoding Arg at position 50 to Arg at position 56 of the N-terminus: 5'-ctcctcagatcacagctccg (SEQ ID NO: 8) as a reverse primer. After pretreatment at 95° C., 5 minutes, 35 cycles of denaturation at 95° C., 30 seconds, annealing at 44° C., 60 seconds, and extension at 72° C., 90 seconds were repeated to amplify the desired gene, followed by extension at 72° C., 10 minutes to give a 185 bp fragment containing the N-terminal region of hamster IGF-1.

Example 2

Determination of the Nucleotide Sequence and Amino Acid Sequence of the cDNA Encoding Hamster IGF-1

The nucleotide sequence of the cloned gene was determined by a DNA sequencer, and the amino acid sequence was further determined from it to confirm that it encodes hamster IGF-1. Thus obtained amino acid sequence is shown in FIG. 1 and SEQ ID NO: 1, and the DNA sequence is shown in SEQ ID NO: 2.

Mature secreted IGF-1 of any species consists of 70 amino acids, but the hamster IGF-1 gene has a unique sequence, which differs from human IGF-1 by 3 amino acids, i.e., P (Human: D) at position 20, I (Human: S) at position 35, and T (Human: A) at position 67 (FIG. 2).

Example 3

Preparation of Modified Hamster IGF-1 Genes and Their IGF-1 Activities (1) Preparation of Modified Hamster IGF-1 genes The secreted hamster IGF-1 gene has a negatively charged amino acid E (glutamate) at position 3 from the N-terminus. Modified hamster IGF-1 genes in which the amino acid at this position was changed into amino acids for positively shifting the polarity were prepared. The introduction of the mutations into the IGF-1 gene was performed by site-directed mutagenesis.

The native hamster IGF-1 gene and modified hamster IGF-1 genes therefrom are designated as E3E (native), E3K (a glutamate-to-lysine change at position 3), and E3S (a glutamate-to-serine change at position 3) (see FIG. 3).

(2) Effects of Native and Modified Hamster IGF-1 on Proliferation Potency and Survival Rate Plasmids for expressing the modified hamster IGF-1 genes (FIG. 4) were constructed and transferred into the parent strain anti-IL-6R antibody-producing CHO cells, and drug-resistant strains were selected by hygromycin to give cell strains stably expressing these genes. The resulting cell strains were subjected to single cell cloning by Limiting Dilution to give clone cells having high proliferation potency in a serum-free medium lacking IGF-1.

ME45 (E3E), MK44 (E3K), and MS19 (E3S) were selected from the clone cells obtained from the differently charged genes E3E, E3K, and E3S and their cell proliferation potencies and survival rates in a serum-free medium lacking IGF-1 in a 100 ml-spinner flask were compared. The parent strain anti-IL-6R antibody-producing cells were also cultured in a medium supplemented or not with human IGF-1 (Long™R³IGF-1) purchased from JRH Biosciences and tested for comparison. After an 100 ml-spinner flask containing 100 ml of a serum-free subculture medium for MRA(anti-IL-6R antibody)-producing cells was conditioned in a $CO_2$ incubator at 37° C. for 1 hour, $3\times10^6$ cells of each type were centrifuged and added. The initial viable density of cells and survival rate were determined in a 1-mL aliquot of the cultures. On and after days 3-7, a 1-mL aliquot was collected at a fixed time and measured for the number of cells and survival rate.

Figure 5:
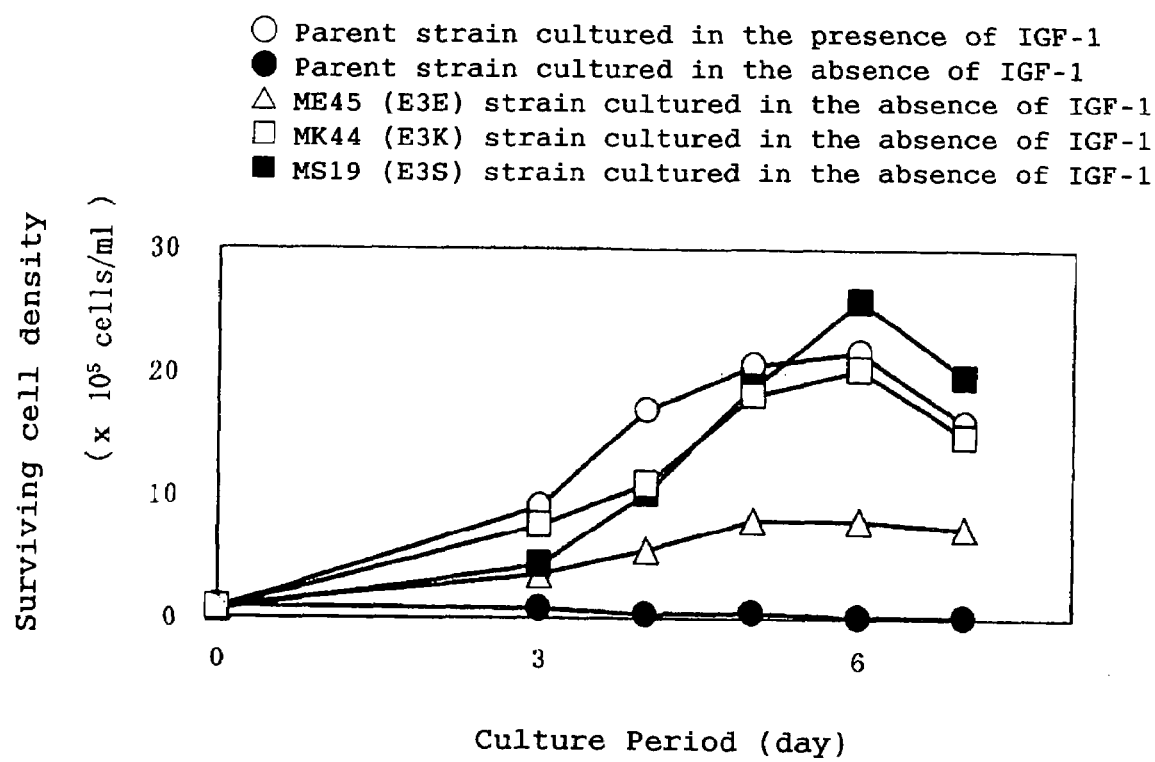
FIG. 5 is a graph showing the effects of native and modified hamster IGF-1 on the proliferation potency.
Figure 6:
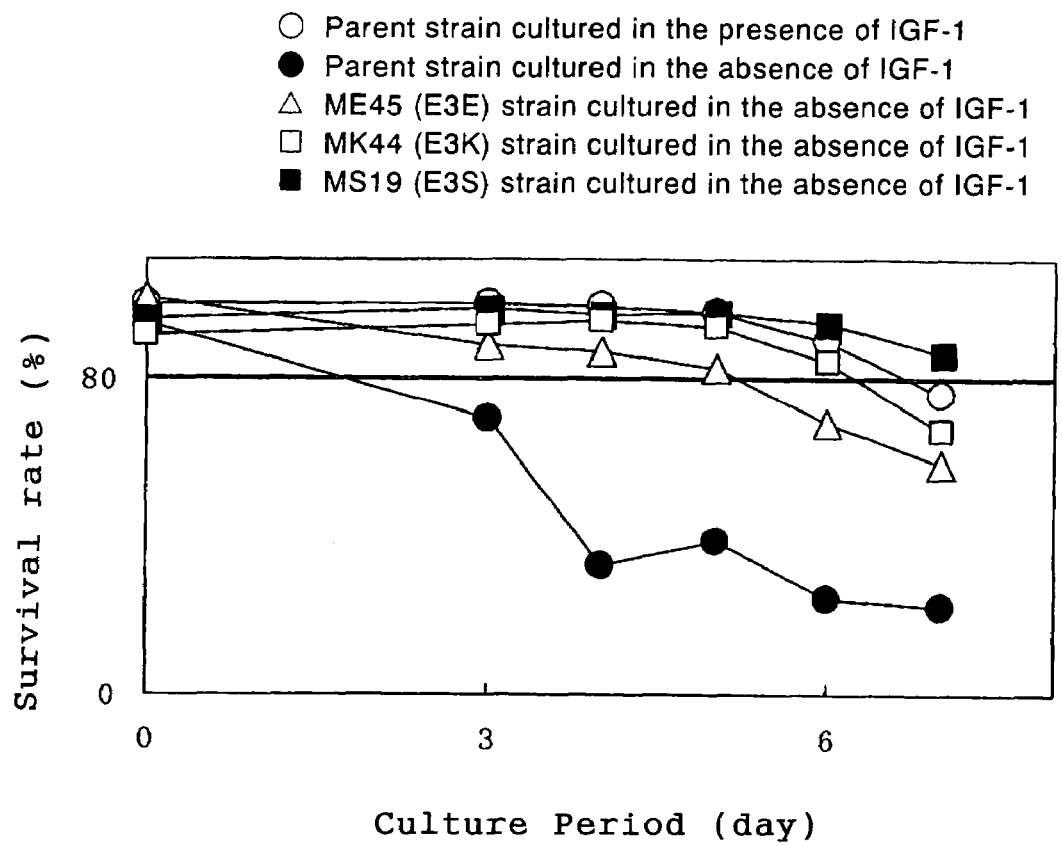
FIG. 6 is a graph showing the effects of native and modified hamster IGF-1 on the survival rate.

The results are shown in FIG. 5 (proliferation potency) and FIG. 6 (survival rate). MS19 (E3S) was shown to the best proliferation potency and also the best survival rate. MS19 (E3S) showed a survival rate of 80% or more even on day 7 of culture. MK44 (E3K) showed the second better results. The parent strain anti-IL-6R antibody-producing cells were not able to grow when they were cultured in the absence of IGF-1.

The proliferation potency of MS19 was prominent during days 3 to 6 of culture, and especially advantageous as shown from the doubling time (MS19; 26.5 hr, MK44; 33.0 hr, ME45; 47.0 hr, anti-IL-6R parent strain; 86.7 hr) and maximum number of cells (MS19; 25.8×10$^5$ cells/ml, MK44; 20.3×10$^5$ cells/ml, ME45; 7.98×10$^5$ cells/ml, anti-IL-6 parent strain; 21.7×10$^5$ cells/ml) during days 4 to 5. The growth behavior of MS19 gently rising and then steeply growing to the late growth phase was ideal for antibody-producing cells. Also as prominent from the comparison of the survival rates on day 7 of culture (MS19; 86.2%, MK44; 66.4%, ME45; 58.1%, anti-IL-6 parent strain; 76.0 hr %), MS19 was the most stable cell strain until the late growth phase.

Example 4

Amounts of Antibodies Produced by Cells Transformed with Hamster IGF-1 (E3S)

To demonstrate that hamster IGF-1 has an antibody-producing potential equal to or higher than that of human IGF-1, the amounts of anti-IL-6R antibodies produced by single clones showing the best growth behavior among the parent strain cells transformed with hamster IGF-1 (E3S) and human IGF-1 (E3S) were compared. A human IGF-1 (E3S)-expressing plasmid was constructed by successively introducing mutations for P20D, I35S and T67A changes using hamster IGF-1 (E3S) as template. In the same manner as described in Example 1, the plasmid was transferred into the parent strain anti-IL6-R antibody-producing CHO cells and hygromycin-resistant cells were selected to give cell strains stably expressing IGF-1 (E3S), whereby cell strains having acquired proliferation potency in a medium lacking IGF-1 were selected. Single clones were obtained by limiting dilution of the cell stranes, and the amounts of antibodies produced in fed-batch cultures of cells transformed with IGF-1 (E3S) having high proliferation potency were compared.

Figure 7:
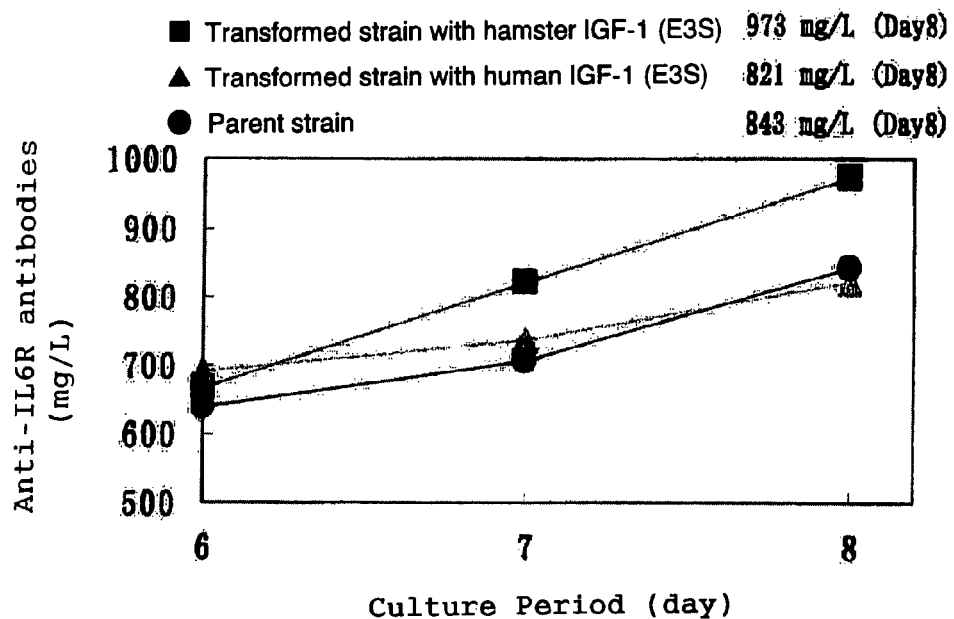
FIG. 7 is a graph showing a comparison of the amounts of antibodies produced in fed-batch cultures of anti-IL6R antibody-producing cells transformed with hamster and human IGF-1 (E3S).

The results are shown in FIG. 7. The amount of antibodies produced by cells transformed with hamster IGF-1 (E3S) was 973 mg/L on day 8 of culture, which was higher than those produced by the parent strain (843 mg/L) and cells transformed with human IGF-1 (E3S) (821 mg/L). It was shown that the cells transformed with the hamster gene produced the highest amount of antibodies in spite of the culture method optimized for the parent strain.

Example 5

Amounts of Antibodies Produced by Cells Transformed with Hamster IGF-1 (E3S)

In addition to Example 4 demonstrating that hamster IGF-1 has an antibody-producing potential higher than that of human IGF-1, antibody-producing potentials of three IGF-1 species including mouse IGF-1 were further compared. A mouse IGF-1 (E3S)-expressing plasmid was constructed by introducing a mutation for a S69A change using hamster IGF-1 (E3S) as template. For comparison among three native IGF-1 (E3E) species in addition to IGF-1 (E3S) mutants in this example, the hamster, human and mouse IGF-1 (E3S) genes were used as templates to construct their native IGF-1 (E3E)-expressing plasmids by introducing a mutation for E3E.

The resulting six IGF-1-expressing plasmids were transferred by electroporation into the parent strain prepared in parallel, and hygromycin-resistant cells were selected to give cell strains stably expressing IGF-1, whereby three cell strains of each group showing the highest growth among cell strains having acquired proliferation potency in a medium lacking IHF-1 (n=3). After one human IGF-1 (E3E) strain became unable to grow during expansion, the experiment was continued with n=2 only for human IGF-1 (E3E) and a total of 17 cell strains were expanded in a 100 ml-spinner flask and then the amounts of antibodies produced in fed-batch cultures were compared.

Figure 8:
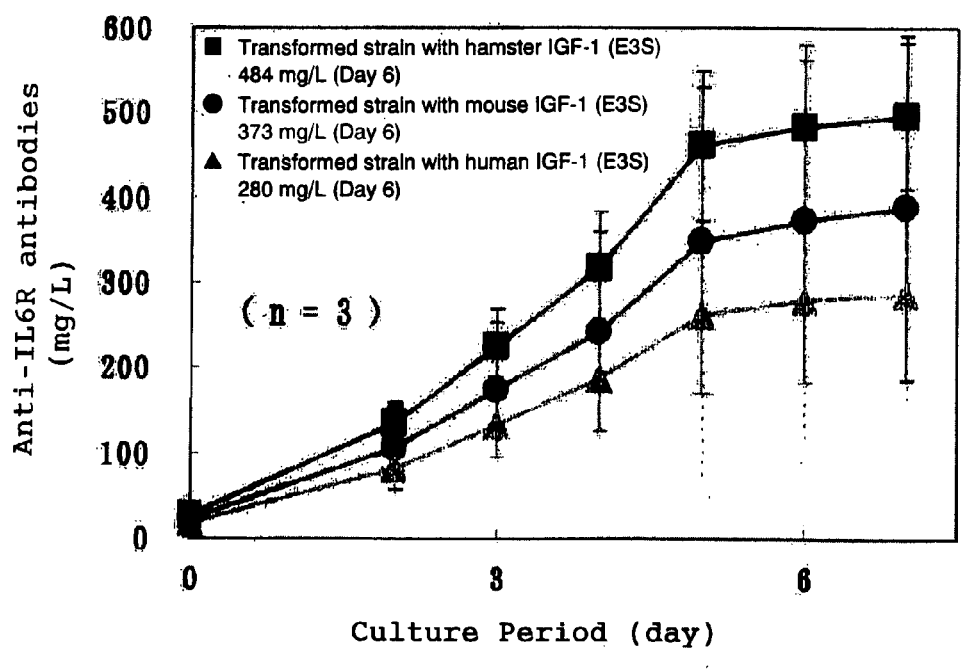
FIG. 8 is a graph showing the amounts of antibodies produced in fed-batch cultures of anti-IL6R antibody-producing cells transformed with hamster, mouse and human IGF-1 (E3S).
Figure 9:
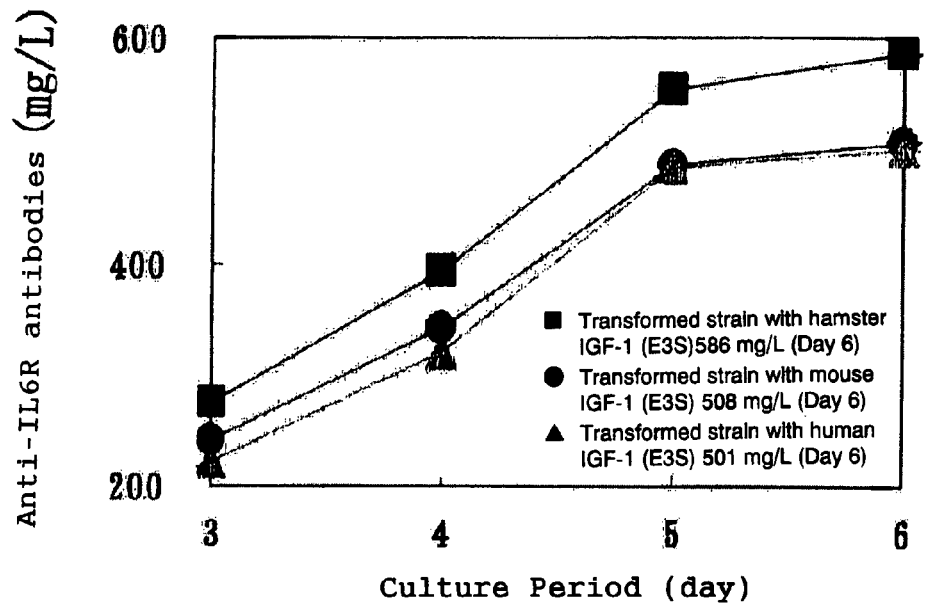
FIG. 9 is a graph showing a comparison of the amounts of antibodies produced by strains having the highest production levels among triple anti-IL6R antibody-producing cells transformed with hamster, mouse and human IGF-1 (E3S).
Figure 10:
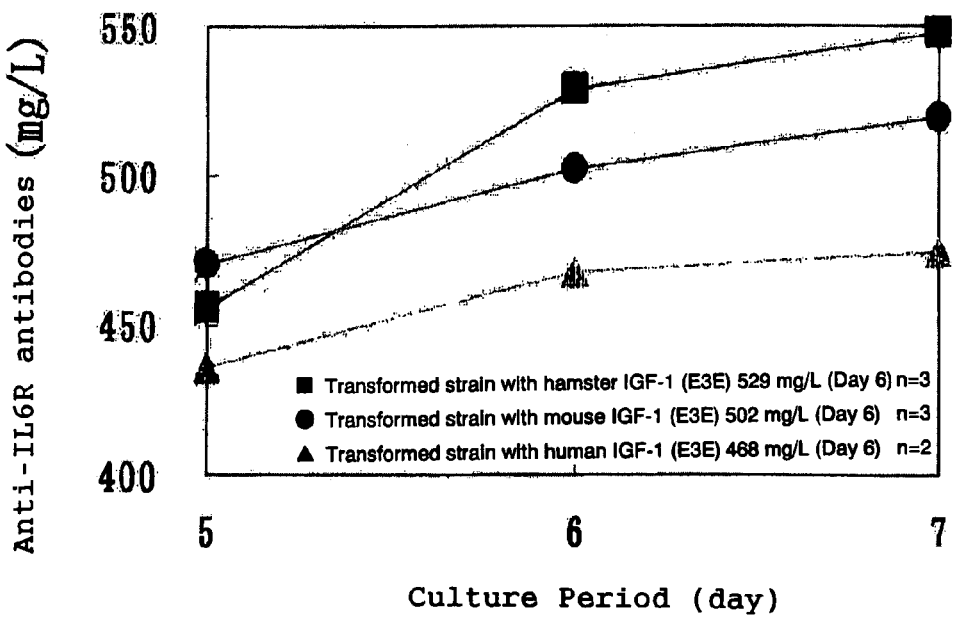
FIG. 10 is a graph showing the amounts of antibodies produced in fed-batch cultures of anti-IL6R antibody-producing cells transformed with hamster, mouse and human IGF-1 (E3E).

FIG. 8 shows the amounts of antibodies produced in fed-batch cultures of cells transformed with hamster, mouse and human IGF-1 (E3S). The average amount of antibodies produced by three strains showing high growth in each group (n=3) was better in the order of hamster>mouse>human. FIG. 9 shows a comparison of strains having the highest antibody-producing levels among the three cell strains transformed with hamster, mouse and human IGF-1 (E3S). In addition to the average amount, the hamster IGF-1 (E3S) transformant was also superior in the amount of antibodies produced by the strain having the highest potential. FIG. 10 shows the amounts of antibodies produced in fed-batch cultures of cells transformed with hamster, mouse and human IGF-1 (E3E). The average amount of antibodies produced by strains transformed with native IGF-1 (E3E) showing high growth was also better in the order of hamster>mouse>human.

The invention claimed is:

1. An isolated DNA that encodes a polypeptide, wherein the polypeptide comprises the amino acid sequence of SEQ ID NO: 1, except for a substitution of the amino acid at position 3 of SEQ ID NO: 1 with serine, lysine or aspartate and wherein the polypeptide has cell proliferation-promoting activity.

2. A vector comprising the DNA of claim 1.

3. An isolated host cell transformed with the vector of claim 2.

4. The host cell of claim 3, which is a Chinese hamster ovary (CHO) cell.

5. A method for preparing a polypeptide comprising:
   (i) harvesting transformants from the host cell of claim 3 or 4 and
   (ii) purifying the polypeptide obtained.

6. An isolated cell for producing a desired protein, said cell transformed with: i) an isolated DNA that encodes a polypeptide, wherein the polypeptide comprises the amino acid sequence of SEQ ID NO:1, except for a substitution of the amino acid at position 3 of SEQ ID NO:1 with serine, lysine or aspartate and wherein the polypeptide has cell proliferation-promoting activity; and ii) an isolated DNA that encodes the desired protein.

7. The cell of claim 6, wherein the DNA encoding the polypeptide and the DNA encoding the desired protein are present on a single vector.

8. The cell of claim 6, wherein the DNA encoding the polypeptide and the DNA encoding the desired protein are present on different vectors.

9. The cell of claim 6, which is a Chinese hamster ovary (CHO) cell.

10. A method for preparing a desired protein, comprising culturing the cell of claim 6.

11. A culture medium comprising:
    i) a polypeptide, wherein the polypeptide comprises the amino acid sequence of SEQ ID NO: 1, except for a substitution of the amino acid at position 3 of SEQ ID NO:1 with serine, lysine or aspartate and wherein the polypeptide has cell proliferation-promoting activity and
    ii) a desired protein.

12. The culture medium of claim 11, wherein the polypeptide is added to the medium.

13. The culture medium of claim 11, wherein the polypeptide is secreted from a host cell.

14. The culture medium of claim 11, which is a serum-free medium or a medium free from any component obtained from mammals, except for the polypeptide.

15. A method for preparing a desired protein, comprising culturing a Chinese hamster ovary (CHO) cell using the culture medium of claim 11.

16. A method for preparing a cell, comprising:
    (a) transferring a DNA encoding a desired protein into a Chinese hamster ovary CHO) cell, and
    (b) transferring a DNA encoding IGF-1(insulin-like growth factor-1) into the cell prepared in (a), to promote cell proliferation and thereby preparing the cell, wherein IGF-1 is a polypeptide comprising the amino acid sequence of SEQ ID NO:1, except for a substitution of the amino acid at position 3 of SEQ ID NO:1 with serine, lysine or aspartate and wherein the polypeptide has cell proliferation-promoting activity.

17. A method for preparing a cell, comprising:
    (a) transferring a DNA encoding a desired protein into a Chinese hamster ovary (CHO) cell;
    (b) selecting a cell expressing the desired protein from the cell prepared in (a); and
    (c) transferring a DNA encoding IGF-1 (insulin-like growth factor-1) into the cell selected in (b), to promote cell proliferation and thereby preparing the cell, wherein IGF-1 is a polypeptide comprising the amino acid sequence of SEQ ID NO:1, except for a substitution of the amino acid at position 3 of SEQ ID NO:1 with serine, lysine or aspartate and wherein the polypeptide has cell proliferation-promoting activity.

18. A method for preparing a cell, comprising:
    (a) transferring a DNA encoding a desired protein and a DNA encoding IGF-1 (insulin-like growth factor-1) simultaneously into a Chinese hamster ovary (CHO) cell, wherein the IGF-1 promotes cell proliferation and the IGF-1 is a polypeptide comprising the amino acid sequence of SEQ ID NO:1, except for a substitution of the amino acid at position 3 of SEQ ID NO:1 with serine, lysine or aspartate; and
    (b) selecting a cell expressing the desired protein from the cell prepared in (a).

19. The method of claim 18, wherein the DNA encoding the desired protein and the DNA encoding IGF-1(insulin-like growth factor-1) are simultaneously transferred into a Chinese hamster ovary (CHO) cell using a single vector containing the DNA encoding the desired protein and the DNA encoding IGF-1.

20. A method for preparing a cell, comprising:
    (a) transferring a DNA encoding IGF-1 into a Chinese hamster ovary (CHO) cell; and
    (b) transferring a DNA encoding a desired protein into the cell prepared in (a), wherein the IGF-1 promotes cell proliferation and the IGF-1 is a polypeptide comprising the amino acid sequence of SEQ ID NO:1, except for a substitution of the amino acid at position 3 of SEQ ID NO:1 with serine, lysine or aspartate.

21. A method for preparing a cell, comprising:
    (a) transferring a DNA encoding IGF-1 into a Chinese hamster ovary (CHO) cell, wherein the IGF-1 promotes cell proliferation and the IGF-1 is a polypeptide comprising the amino acid sequence of SEQ ID NO:1, except for a substitution of the amino acid at position 3 of SEQ ID NO:1 with serine, lysine or aspartate;
    (b) transferring a DNA encoding a desired protein into the cell prepared in (a); and
    (c) selecting a cell expressing the desired protein from the cell prepared in (b).

* * * * *

SEQUENCE LISTING

```
<160> NUMBER OF SEQ ID NOS: 10

<210> SEQ ID NO 1
<211> LENGTH: 70
<212> TYPE: PRT
<213> ORGANISM: Cricetinae sp.

<400> SEQUENCE: 1

Gly Pro Glu Thr Leu Cys Gly Ala Glu Leu Val Asp Ala Leu Gln Phe
 1               5                  10                  15

Val Cys Gly Pro Arg Gly Phe Tyr Phe Asn Lys Pro Thr Gly Tyr Gly
            20                  25                  30

Ser Ser Ile Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60
```

```
Lys Pro Thr Lys Ser Ala
 65                 70

<210> SEQ ID NO 2
<211> LENGTH: 242
<212> TYPE: DNA
<213> ORGANISM: Cricetinae sp.
<220> FEATURE:
<221> NAME/KEY: CDS
<222> LOCATION: (13)..(225)

<400> SEQUENCE: 2
tttgccacag ct gga cca gag acc ctc tgc ggg gct gag ctg gtg gat gct       51
              Gly Pro Glu Thr Leu Cys Gly Ala Glu Leu Val Asp Ala
                1               5                  10 ctt caa ttc gtg tgt gga cca agg ggc ttt tac ttc aac aag ccc aca         99
Leu Gln Phe Val Cys Gly Pro Arg Gly Phe Tyr Phe Asn Lys Pro Thr
     15                  20                  25 ggc tat ggc tcc agc att cgg agg gca cct cag aca ggc att gta gat        147
Gly Tyr Gly Ser Ser Ile Arg Arg Ala Pro Gln Thr Gly Ile Val Asp
 30                  35                  40                  45 gag tgc tgc ttc cgg agc tgt gat ctg aga aga ctg gag atg tac tgt        195
Glu Cys Cys Phe Arg Ser Cys Asp Leu Arg Arg Leu Glu Met Tyr Cys
                 50                  55                  60 gcc ccc ctc aag cct aca aaa tcg gcc cgctctatcc gtgcccagcg              242
Ala Pro Leu Lys Pro Thr Lys Ser Ala
                 65                 70

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctcttcagt tcgtgtgtgg                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcctcagat cacagctccg                                                   20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acaggctatg gctccagcat t                                                 21

<210> SEQ ID NO 6
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 6
tgagtcttgg gcatgtcagt g                                               21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcttgctca cctttaccag                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctcctcagat cacagctccg                                                 20

<210> SEQ ID NO 9
<211> LENGTH: 70
<212> TYPE: PRT
<213> ORGANISM: Homo sapiens

<400> SEQUENCE: 9

Gly Pro Glu Thr Leu Cys Gly Ala Glu Leu Val Asp Ala Leu Gln Phe
  1               5                  10                  15

Val Cys Gly Asp Arg Gly Phe Tyr Phe Asn Lys Pro Thr Gly Tyr Gly
             20                  25                  30

Ser Ser Ser Arg Arg Ala Pro Gln Thr Gly Ile Val Asp Glu Cys Cys
         35                  40                  45

Phe Arg Ser Cys Asp Leu Arg Arg Leu Glu Met Tyr Cys Ala Pro Leu
     50                  55                  60

Lys Pro Ala Lys Ser Ala
 65                  70

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tttttttttt tttttttttt tttt                                            24
```